(12) United States Patent
Zamoyski

(10) Patent No.: US 6,355,251 B1
(45) Date of Patent: Mar. 12, 2002

(54) COMPOSITIONS AND METHODS FOR EPIDERMAL CHEMEXFOLIATION

(76) Inventor: Mark Zamoyski, 988 Foothill Dr., San Jose, CA (US) 95123

( * ) Notice: Subject to any disclaimer, the term of this patent is extended or adjusted under 35 U.S.C. 154(b) by 0 days.

(21) Appl. No.: 09/965,198

(22) Filed: Sep. 26, 2001

Related U.S. Application Data

(63) Continuation-in-part of application No. 09/459,394, filed on Nov. 24, 1999, which is a continuation-in-part of application No. 09/333,832, filed on Jun. 15, 1999, now abandoned.

(51) Int. Cl.[7] .......................... A61K 35/78; A61K 7/00
(52) U.S. Cl. ............................ 424/195.15; 424/195.16; 424/401
(58) Field of Search .............................. 424/195.15, 401

(56) References Cited

U.S. PATENT DOCUMENTS 4,744,981 A    5/1988  Pavanasasivam
4,906,452 A    3/1990  Sivam

OTHER PUBLICATIONS

Okazaki et al., Agricultural and Biological Chemistry (1989) vol. 53 pp. 1441–1443.
Okazaki et al., Agricultural and Biological Chemistry (1988) vol. 52 pp. 795–801.
Dearborn et al., Morbidity and Mortality Weekly Report Dec. 9, 1994/ vol. 43/ No. 48 pp. 881–883.
US Amriid, "Understanding the Threat" Website Printout (on Aug. 27, 1994) pp. 2–3 for LD50 of T–2.
Magnuson et al, Canadian Journal of Physiology and Pharmacology (1987) vol. 65 No. 5 p. 799 for LD50 of T–2.
Kuwahara et al. eMedicine Journal, May 20, 2000 vol. 1, No. 5, 6 pages; Summary of Prior Art Compositions & Methods on pp. 5–6.

*Primary Examiner*—Leon B. Lankford, Jr.
*Assistant Examiner*—Susan D. Coe

(57) ABSTRACT

Sesquiterpene epoxide compounds (trichothecenes) and methods for administering such compounds to chemexfoliate selected epidermal cell populations are disclosed.

4 Claims, 2 Drawing Sheets

COMPOSITIONS AND METHODS FOR EPIDERMAL CHEMEXFOLIATION

This application is a continuation-in-part of U.S. patent application Ser. No. 09/459,394, filed Nov. 24, 1999, which is a continuation-in-part of U.S. patent application Ser. No. 09/333,832, filed Jun. 15, 1999, now abandoned.

BACKGROUND—SUMMARY

The current invention proposes topical administration of therapeutically effective doses of certain sesquiterpene epoxides (trichothecenes) to chemexfoliate selected areas of the epidermis.

BACKGROUND

Chemexfoliation has been around since the days of ancient Egypt with lactic acid from sour milk used as part of a skin rejuvenation regimen. The middle ages saw tartaric acid from old wine used for the same purpose. Modern day chemical peeling includes such pioneers as P. G. Unna who first described properties of salicylic acid, resorcinol, phenol, and trichloroacetic acid. Baker and Gordon developed deep peeling agents in the 1960s. Alpha and Beta hydroxy acids appeared over the last several decades as mild exfoliants available in many commercially available skin care products. The primary application of chemexfoliation has been, and remains today, rejuvenation of the skin by destruction or damage to the epidermis and sometimes also the dermis.

PRIOR ART TREATMENTS

Prior art chemexfoliants in use today can be grouped into three categories; Superficial Peeling Agents, Medium Depth Peels, and Deep Peels.

Superficial Peeling Agents

Trichloroacetic acid (TCA) 10–35% is safe at lower concentrations. At higher concentrations (>50%) it has a tendency to scar.

Jessner's peel is a combination of salicylic acid (14%), lactic acid (14%), and resorcinol (14%) in alcohol.

Salicylic acid has been used for several decades and is found in various medications ranging from 4% to 17% concentrations.

Carbon Dioxide uses a solid block of CO2 ice dipped in an acetone-alcohol mixture and applied to the skin for 5–15 seconds depending on the desired depth.

Alpha hydroxy acid peels include lactic acid, glycolic acid, tartaric acid and malic acid. Various concentrations can be purchased ranging from 10% to 70% concentrations.

Medium Depth Peels

Combinations peels such as CO2 and TCA 35%, Jessner's and TCA 35%, and Glycolic and TCA 35% are currently being used.

TCA 50% is seldom used today because of risk of scarring.

Full strength phenol (88%) is very caustic an causes immediate keratin agglutination preventing further penetration.

Pyruvic acid is also rarely used today because of difficulty in controlling depth of penetration. An ethyl pyruvate is currently being developed to overcome this issue.

Deep Peels

The Baker Gordon peel is one of the most effective peeling agents currently available. The phenol produces a layer of collagen that is thicker than that produced by laser. However the Baker Gordon formula is not often used today because of laser resurfacing technology.

COMPOSITIONS OF PRESENT INVENTION

The compositions proposed under present invention are not acids nor do they employ freezing. They are protein synthesis inhibitors (PSIs). Accordingly a brief background about protein synthesis and cellular function is presented.

The most fundamental function a cell is protein synthesis (i.e. expression of its DNA). Proteins make up ~60% of a dry cell's mass by weight. In very broad and general terms, as cells mature and differentiate in the body, they reach an equilibrium in protein synthesis and protein degradation and settle down to perform their given function in this relative state of homeostasis. There are two notable exceptions that cause massive perturbations to this homeostasis: 1) when a cell is called upon to grow and divide and 2) when certain secretory cells are called upon to produce large amounts of proteins for secretion. Although the cell signaling signaling pathways, intracellular transduction pathways, and spectrum of protein(s) to be produced are quite different in growth versus secretion, normal growth and secretion events share one major similarity in their end result: massively accelerated protein synthesis. A cell that is called on to grow (cycling cell) has as much as 5 times the protein synthesis activity of a non cycling cell and needs between 2,000 and 5,000 different enzymes and structural proteins to grow and divide. Likewise, secretory cells such as those of the immune system become protein factories producing massive amounts of antibodies, mediators, growth factors, or other proteins when stimulated to do so.

There are also abnormal conditions such as cancer and viral infections that share the same property of hyperactive protein synthesis versus normal quiescent cells. Cancer is a growth and divide type event, and even though the signaling mechanism is different in that it is self-induced intracellularly by several genetic mutations, the end result is also hyperaccelerated protein synthesis characteristic of a cycling cell. Viruses invade a cell, parasitize the host cellular machinery, and convert the cell into a factory producing massive amounts of viral proteins, much like a secretory cell.

Inhibiting protein synthesis affects cells in a dose dependent manner and affects actively cycling cells differently than non cycling cells. At low doses, protein synthesis inhibitors (PSIs) stop actively cycling cells from cycling without killing them (hereinafter referred to as inhibitory or G zero inducing dose). Inhibitory doses also stop hyperaccelerated protein synthesis by secretory cells. At moderate doses PSIs exhibit toxicity to actively cycling cells (hereinafter referred to as the cytotoxic dose). At high doses, PSIs exhibit toxicity to all cells (hereinafter referred to as the toxic dose).

There are roughly 210 epithelial cell types in the body, and only a small handful are normally actively cycling. These include the epidermis, hair, bone marrow, and gastrointestinal mucosa. Epidermal cells cycle on a roughly 24 hour clock and as such would be susceptible to cytotoxicity from PSIs at dose levels not toxic to normal non rapidly proliferating cells. Non nucleated cells such as the non nucleated epidermal squames at the very top of the epidermis would not be affected. The collagen matrix below the epidermis would not be affected. This presents the opportunity for a highly selective epidermal chemexfoliation of the living epidermal cells sandwiched between the epidermal squames on top and the collagen on bottom.

NOVELTY AND UNOBVIOUSNESS OVER PRIOR ART

Novelty and Unobviousness—Overview

Present invention takes a fairly unobvious view and considers the epidermis a "super cancer". Epidermal basal cells cycle on a roughly 24 hour clock. By contrast, if tumor cells cycled on a 24 hour clock a human would be dead in under a month from the time the tumor was initially detected. Starting with a fairly tiny, clinically undetectable, initial tumor of ~1 Million cells (i.e. 1 μl mass) and growing it to lethal burden at around a Trillion cells (1 L mass), requires only about 20 cell cycles of all the tumor cells (i.e. 1 M, 2,4,8,32,64,128,256,512,1 Bil, 2,4,8,16,32,64, 128, 256,512, 1 Tril.).

Novelty and Unobviousness Over Prior Art Use of Trichothecene

Prior art has attempted to use trichothecene against hyperproliferative conditions such as cancer, however they have failed. Anguidine, a simple trichothecene, was tested against cancer and abandoned after Phase II testing showed a low tumor response and considerable hematologic toxicity. Prior arts attempt to remedy this failure are embodied in U.S. Pat. Nos. 4,906,452 and 4,744,981 which propose conjugates of trichothecene with monoclonal antibodies to enhance delivery to the tumor and glycosylation of trichothecene to increase blood solubility. Present invention takes a novel and unobvious approach that is exactly opposite to prior art in several respects. First, present invention reverses direction of administration (i.e. administered from tissue side to blood versus prior arts direction of blood to tissue). Second, present invention embraces the non specific internalization properties to deliver the greatest doses to tissues it is applied to and depending on those tissues to retain the trichothecene, preventing it from reaching general circulation (versus prior arts targeted delivery by monoclonal antibodies). Third, present invention embraces the use of macrocyclic trichothecene (versus simple trichothecenes in prior art) because the macrocyclic ring enhances rapid non specific internalization further enhancing localization and preventing entry into the blood. Fourth, present invention embraces blood insolubility to prevent entry into the blood (versus prior art glycosylation).

The one nice thing that can be said about chemotherapeutics such as trichothecene is that they kill cleanly because they induce apoptosis. Trichothecenes are cytotoxic to rapidly dividing cells because they interfere with the large burst of protein synthesis that are critical at various points in the cell cycle. In response to this type of intracellular damage or disruption the cell invokes a method of cell death known as apoptosis. Similarly, locally toxic doses proposed under present invention also kill non cycling epidermal cells, from the inside, by preventing synthesis of proteins necessary to maintain cell viability. Apoptosis is a specialized type of cell death the does not initiate the massive immune "injury response" that cutting, freezing (which ruptures the cell membrane through ice crystal formation), or acid destruction does.

Novelty and Unobviousness Over Prior Art Chemexfoliants

Since neither non nucleated epidermal squames at the very top of the epidermis nor the collagen matrix below the epidermis is destroyed by protein synthesis inhibition, compositions of present invention provide a unique opportunity for a highly selective epidermal chemexfoliation of the living epidermal cells sandwiched between the epidermal squames on top and the collagen on bottom. Compositions of present invention are a much "cleaner kill" over prior art as they do not cause widespread rupturing of the cell membranes and spillage of intracellular contents. Thus, compositions of present invention would tend to cause much less pain and inflammation relative to prior art compositions which use acids or combinations of acids (see eMedicine Journal summary of prior art enclosed).

Lastly, present invention will also provide novel treatment methods for conditions not currently treated or treatable by prior art chemexfoliants including, but not limited to, epidermal conditions such as Kaposi's sarcoma warts, moles, and basal and squamous cell carcinomas.

SUMMARY OF THE INVENTION

Present invention proposes epidermal chemexfoliation by topical administration of therapeutically effective doses of trichothecene.

BRIEF DESCRIPTION OF DRAWING FIGURES

FIG. 1A shows the hyperactive protein synthesis inhibiting dose profile in human cells of Roridin A, a representative macrocyclic trichothecene.

FIG. 1B shows the hyperactive protein synthesis inhibiting dose profile in human cells of Satratoxin G, a representative macrocyclic trichothecene.

FIG. 2A shows the hyperactive protein synthesis inhibiting dose profile in human cells of T-2, a representative simple trichothecene.

FIG. 2B shows the hyperactive protein synthesis inhibiting dose profile in human cells of DAS, a representative simple trichothecene.

DETAILED DESCRIPTION OF THE INVENTION

The treatments disclosed below involve topical administration of biologically active trichothecenes the effectuate the cell death of targeted epidermal cell populations. Materials and methods for achieving this are described below.

Trichothecenes Defined

Fungi of the genera Fusarium, Myrotecium, Trichoderma, Stachybotrys and others produce *Trichothecene mycotoxins*. Trichothecenes constitute a family of fungal sesquiterpene epoxides that inhibit protein synthesis. *Trichothecene mycotoxins* are low molecular weight (250–700 daltons), non volatile compounds, and of over 150 trichothecenes have been identified. There are two broad classes: those that have only a central sesquiterpenoid structure and those that have an additional macrocyclic ring (simple and macrocyclic trichothecenes, respectively). As used in this application, "therapeutics", "biologically active agent", or "trichothecene" are defined as either simple or macrocyclic trichothecenes and include molecules of the following general chemical formulas: Simple trichothecenes are categorized into three groups with the following chemical formulas:

Group A

Wherein $R_1$ is H, OH, or $$O-\overset{O}{\underset{\|}{C}}-CH_3;$$

$R_2$ is H, OH, or $$O-\overset{O}{\underset{\|}{C}}-CH_3;$$

$R_3$ is H, OH, or $O-C-CH_3$;

$R_4$ is H, or OH; and $R_5$ is H, OH, $$O-\overset{O}{\underset{\|}{C}}-CH_3 \text{ or } \overset{O}{\underset{\|}{C}}-O-CH_2(CH_3)_2.$$

Group B

[chemical structure with $R_1$, $R_2$, $R_3$, $R_4$, CH$_2$]

Wherein $R_1$ is H, OH, or $$O-\overset{O}{\underset{\|}{C}}-CH_3;$$

$R_2$ is H, OH, $$O-\overset{O}{\underset{\|}{C}}-CH_3 \text{ or } O-\overset{O}{\underset{\|}{C}}-CH=CH-CH_3;$$

$R_3$ is H, OH, or $$O-\overset{O}{\underset{\|}{C}}-CH_3;$$

$R_4$ is H, OH, or $$O-\overset{O}{\underset{\|}{C}}-CH_3;$$

Group C

[chemical structure with R']

Wherein

R' is OH or $$O-\overset{O}{\underset{\|}{C}}-CH=CH-CH_3.$$

Macrocyclic Trichothecenes can be described by the following general chemical formulas:

[chemical structure with $R_1$, $R_2$, R']

Wherein $R_1$ is $$OH, \text{ or } O\overset{O}{\underset{\|}{C}}-CH_3;$$

$R_2$ is H, OH, $$O-\overset{O}{\underset{\|}{C}}-CH3$$

or OCOCH$_2$CH(CH$_3$)$_2$; and

R' is any molecule composed predominantly, or in its entirety, of combinations of C, H, and O:

Some representative examples of R' include:

Satratoxin H

[chemical structure]

Satratoxin G

[chemical structure]

or molecules of the following general formula:

Wherein

R₁ is H, OH, or $$O-\overset{O}{\underset{\|}{C}}-CH_3;$$

R₂ is H, OH, $$O-\overset{O}{\underset{\|}{C}}-CH_3$$

or OCOCH₂CH(CH₃)₂; and

R' is any molecule composed predominantly, or in its entirety, of combinations of C, H, and O.

A more comprehensive listing of trichothecenes is included in U.S. Pat. Nos. 4,744,981 and 4,906,452, incorporated herein by reference.

Trichothecenes are fast acting potent inhibitors of protein synthesis in eucaryotic cells. Their main effects are on rapidly proliferating tissues such as bone marrow, skin, mucosa epithelia, and germ cells. The sesquiterpenoid ring binds to ribosomes, inhibiting protein synthesis. The macrocyclic ring enhances cell binding and internalization.

Trichothecenes are invisible to the immune system since they neither contain nor produce amino acids. Since trichothecene molecules contain only carbon, hydrogen, and oxygen they are not subject to proteolytic degradation. U.S. Pat. No. 4,906,452 (column 11 first paragraph) further discloses that some studies of the rates at which certain trichothecenes are converted into biologically inactive molecules (apotrichothecenes) found that macrocyclic trichothecenes are inactivated quite slowly and only by intracellular acid catalysis as might occur in lyzosomes.

Trichothecenes are extremely stable to heat and ultraviolet light inactivation. Heating to 500° F. for 30 minutes is required for inactivation. Brief exposure to NaOH destroys toxic activity. These substances are relatively insoluble in water but are highly soluble in ethanol, methanol, and propylene glycol.

Preferred Trichothecenes

Macrocyclic trichothecenes are preferred for use in present invention because they are relatively insoluble in blood and because the macrocyclic ring enhances cellular binding and internalization which tends to localize them more quickly and prevent their entry into general circulation.

An excellent in vivo example of this is the Cleveland Infant Model. The Cleveland infant model showed the reluctance of macrocyclic trichothecenes to enter the blood stream, and instead their tendency to localize into the epithelium with which they initially came into contact with.

The Cleveland Infant Model

The cluster of infant hemosiderosis in Cleveland (MMWR report) demonstrated, in vivo, in humans, the ability of certain macrocyclic trichothecenes to localize in tissue without appreciably entering general circulation. Adults and infants were subjected (inadvertently) to airborne (cytotoxic) concentrations of trichothecenes produced naturally by the fungus *Stachybotrys atra*. Trichothecenes produced by *S. Atra* include satratoxins H, G, F, roridin E, verrucarin J, and trichoverrols A and B.

The mean age of the infants was ~10 weeks old (range 4–16 weeks). At this age, the lungs of infants are growing at an accelerated rate, and the destruction of lung tissue clearly indicated cytotoxic airborne concentrations. In the infants examined, despite the acute pulmonary hemorrhage/hemosiderosis, the inhaled trichothecenes localized in the lung epithelium and did not enter circulation where they would have caused systemic cytotoxicity. Laboratory findings on admission showed a normal white blood cell count (median=13.8 cells/cubic mm) in the infants. Red blood cell counts were consistent with the blood loss from the hemosiderosis. No other source of bleeding (i.e. gastrointestinal or nasopharyngeal) was identified during endoscopic evaluation. This demonstrates both the reluctance of these macrocyclic trichothecenes to enter the blood stream as well as the tendency for them to localize into the epithelium with which they first came into contact with.

The likely molecular basis for the "localization" of these trichothecenes is their ability to be rapidly internalized into cells because of their macrocyclic ring combined with their insolubility in blood, which would tend to keep them out of the circulatory system. The incredibly small size of trichothecenes (~1 nm or less) allows them to travel between cells (~2–4 nm spacing). Once internalized they can travel through gap junctions. Gap junctions allow molecules smaller than 1000 daltons (~1.5 nm in diameter) to pass between connected cells and trichothecenes are comfortably under the size limitation at 250–700 daltons. Gap junction travel would tend to further localized trichothecenes within the organ or other connected tissue mass.

It is likely the inhaled trichothecenes are somewhat "trapped" between the lumen of the lungs on one side and the circulatory system on the other side, in which they are insoluble. In between this is the lung tissue in which they eventually internalized—in virtually the same way they would be expected to act when applied topically to the skin—internalizing in the skin without appreciably entering general circulation.

Although there have been studies on the rates at which trichothecenes are intracellularly converted into biologically inactive apotrichothecenes, the Cleveland infant model also provides a rare glimpse of how slowly macrocyclic trichothecenes are inactivated, in vivo. All infants survived the first hospitalization and were discharged without evidence of hemoptysis after a median length of stay of 10 days, indicating an inactivation time in the ballpark of 10 days.

Preparation of Trichothecenes

Fungi can be grown in culture and the trichothecenes extracted by centrifugal partition chromatography as described in Tani et. al. and described in other literature such as Onji et. al. (Onji, Y., Aoki, Y., Yamazoe, Y., Dohi, Y., and Moriyamam, T., 1988 *Isolation of nivalenol and fusarenon-X from pressed barley culture by centrifugal* partition chromatography, *Journal Liquid Chromatography,* 11:2537–2546) or Jarvis et al. (Jarvis, B. B., R. M. Eppley, and E. P. Mazzola, 1983 *Chemistry and Bioproduction of the Macrocyclic Trichothecenes,* p 20–38. In *Y. Ueno, Trichothecenes: chemical, biological, and toxicological aspects,* vol 4. Elsevier Science Publishing Inc., New York) or Sorensen et al. (Sorenson, W. G., Frazer, D. G., Jarvis, B. B., Simpson, J., and Robinson, V. A., *Trichothecene Mycotoxins in Aerosolized Conidia of Stachybotrys atra,* June 1987 *Applied and Environmental Microbiology,* Vol. 53 No. 6, p. 1370–1375) where *S. atra* was grown on sterile rice, autoclaved, dried, and then aerosolized by acoustic vibration and collected on glass-fiber filters and extracted with 90% aqueous methanol.

Alternatively, certain trichothecene mycotoxins can be purchased from companies such as Sigma Chemical Co. St. Louis Mo., USA or Wako Pure Chemical Industries, Ltd., Japan, or Wellcome Research Labs, Buckinghamshire, England or Boehringer-Mannheim, Manheim, West Germany.

Method of Administration

Preferred embodiment of current invention administers trichothecenes by topical application, mixed with either ethanol, methanol, propylene glycol, or dimethyl sulfoxide. The latter serve no biological role other than to act a vehicle to facilitate uniform distribution of the trichothecene to a given area of skin. These mixtures are hereinafter referred to as "therapeutic compositions" or "pharmaceutical compositions" or "compositions" and nothing in this application is intended to limit trichothecene from being mixed with any suitable substance that may facilitate administration, uniformity of distribution, enhance absorption, increase efficacy, or with other trichothecenes or any other substances that serve any other beneficial purpose, the aforementioned combinations also called "therapeutic composition" or "pharmaceutical compositions" of present invention. The term "therapeutics" or "therapeutics of present invention" is generally intended to refer to the biologically active trichothecene(s). Preferred embodiment use a variety of devices to facilitate application of therapeutics of present invention such as eye droppers, brushes, pressurized tubes, syringes, roller ball applicators, to name a few. Other devices, either currently existing, or to be developed in the future could also be employed. As an example the preferred embodiment for the future application of therapeutics of present invention envisions devices (e.g. low velocity "atomizers") capable of accelerating therapeutics or pharmaceutical compositions of present invention to velocities capable of instantaneous epidermal penetration and distribution.

Dose Determination

Figures 1A, 1B:
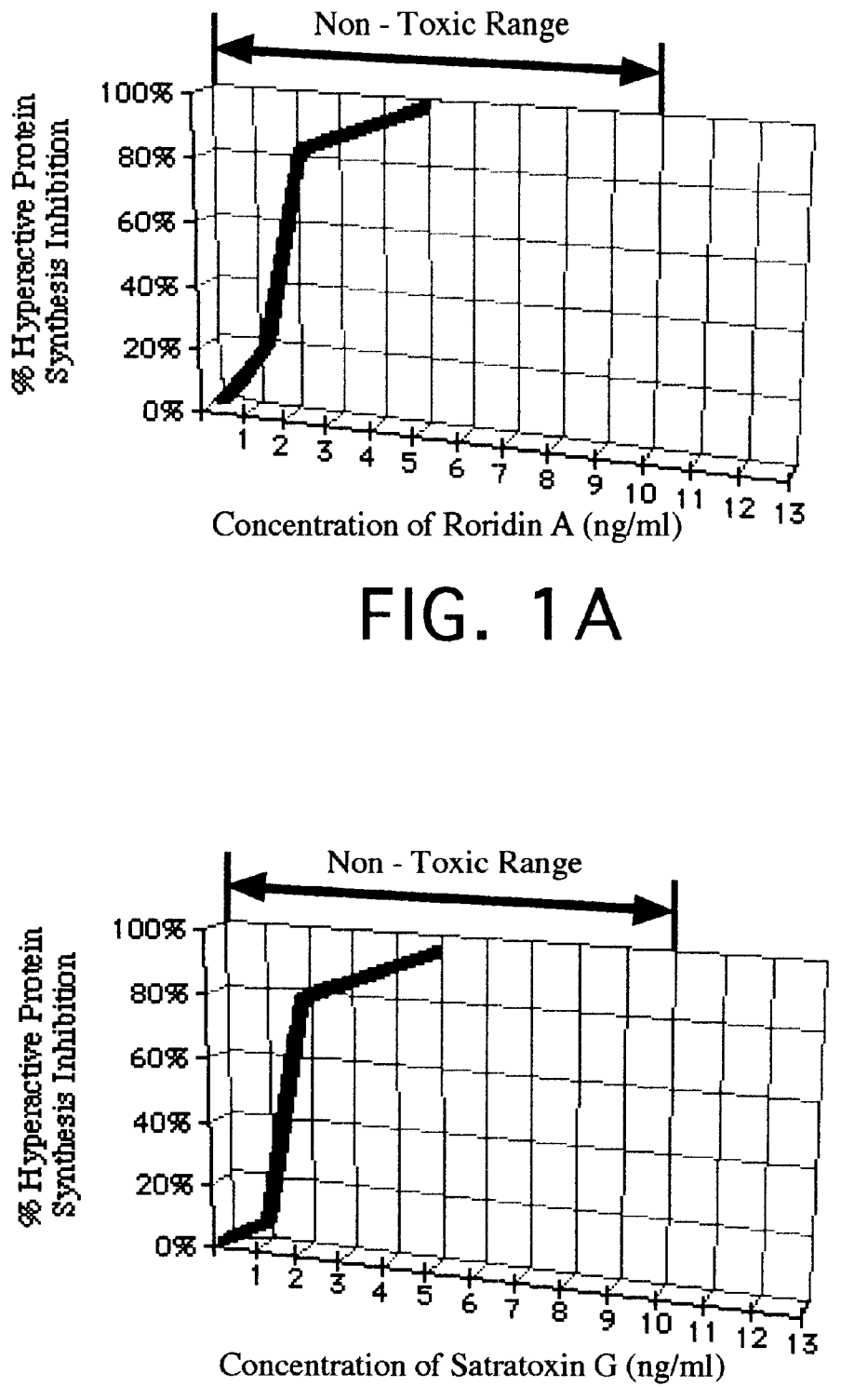
Figures 2A, 2B:
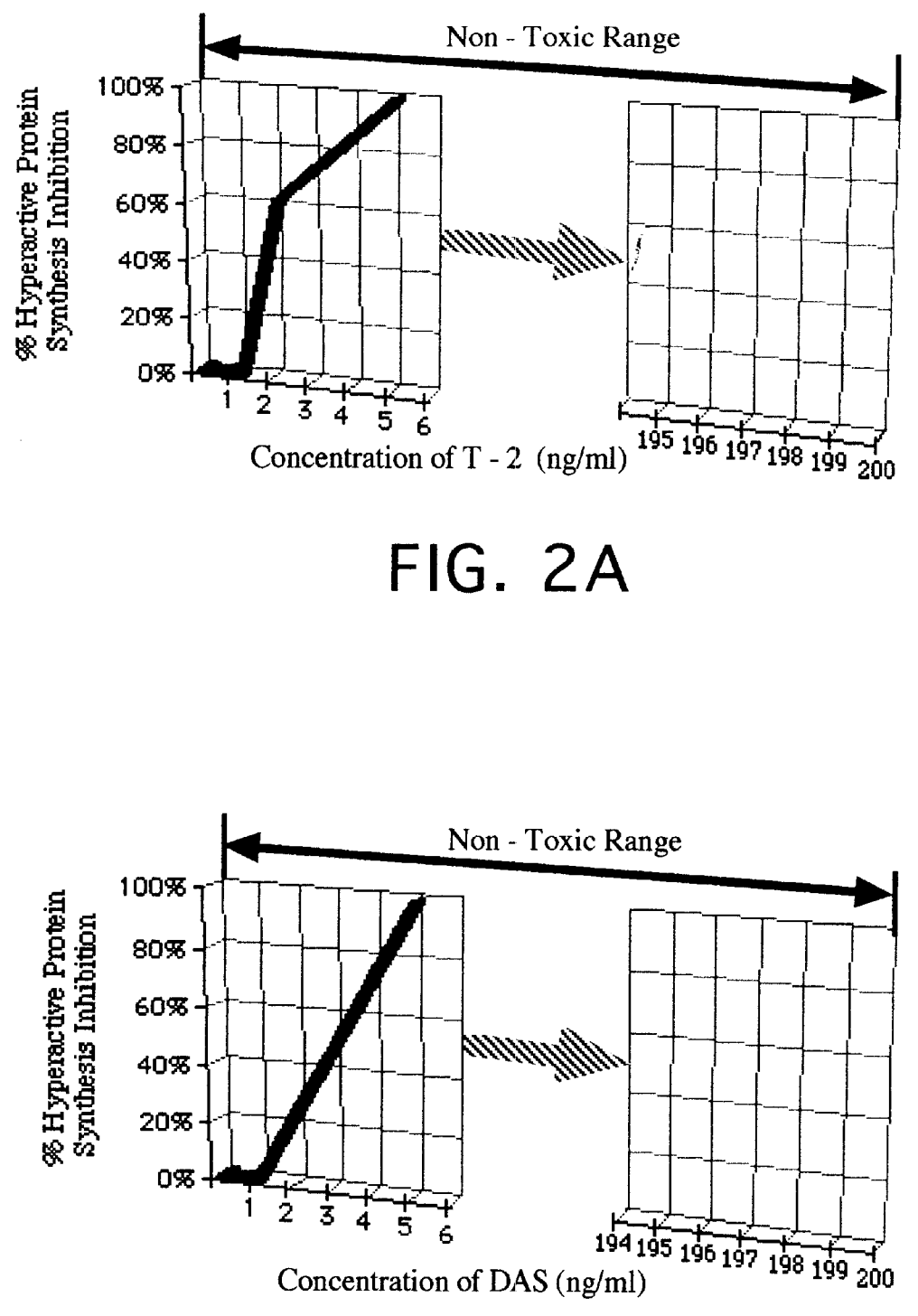

The hyperactive protein synthesis inhibiting profiles were constructed from data collected from in vitro experiments using human epidermoid cells, virally infected with HSV-2 to induce a hyperactive state of protein synthesis, and conducted and reported by Okazaki et. al. in the attached Journal of Agricultural and Biological Chemistry articles. Since the Okazaki experiments were to determine viral inhibition properties, the data has been reformatted for relevance to present invention in establishing baseline "safe" levels. Stated data points were taken from Okazaki's text, other data points were read from the graph, the rest were computed by linear interpolation between the aforementioned data points. FIGS. 1A and 1B show the hyperactive protein synthesis inhibiting dose profile of roridin A and satratoxin G, respectively. Both roridin A and satratoxin G are macrocyclic trichothecenes. By ~5 ng/ml both had inhibited 99 + % of the hyperactive protein synthesis. Both did not reduce cell viability at concentrations of 10 ng/ml or less, hereinafter referred to as the maximum Non Toxic Concentration or $NTC_{max}$. Toxicity started above 10 ng/ml, and concentrations above the $NTC_{max}$ are hereinafter referred to as Toxic Concentrations, or TC, with $TC_{min}$ defined as a concentration just above $NTC_{max}$, or greater than 10 ng/ml for roridin and satratoxin. FIGS. 2A and 2B show the hyperactive protein synthesis inhibiting dose profile of T-2 and DAS, respectively. Both T-2 and DAS are simple trichothecenes. By doses of 5 ng/ml both had inhibited ~99% of hyperactive protein synthesis. Neither reduced cell viability at concentrations up to 200 ng/ml. These dosages would be further refined and scrutinized by in vivo testing in suitable animal models or in Phase I and II clinical trials on humans as required by the FDA.

TABLE 1

| | Trichothecene Concentrations (ng/ml) | | | | | |
|---|---|---|---|---|---|---|
| | Protein Synthesis Inhibition | | | | | |
| | 50% | 80% | 85% | 90% | 99+% | $NTC_{max}$ |
| Roridin A | 1.4 | 2.0 | 2.5 | 3.3 | 5.0 | 10 |
| Satratoxin G | 1.5 | 2.4 | 3.2 | 3.9 | 5.0 | 10 |
| T-2 | 1.6 | 3.5 | 3.8 | 4.3 | 5.0 | 200 |
| DAS | 2.3 | 4.0 | 4.2 | 4.5 | 5.0 | 200 |

Two broad methods may be employed to determine dosage for use in epidermal chemexfoliation. Method 1 uses a selected epidermal TC to be achieved, computes the volume of skin involved, and determines the appropriate amount of a given concentration of solution to apply. Method 2 chooses a selected blood safety level and works backward to compute a dose that, under a worst case scenario, if it completely enters the blood stream will not exceed the selected blood NTC level. Preferred embodiment of present invention uses Method 2 however nothing in this application or its related claims is intended to limit the ability to use either Method 1 or Method 2 or any other suitable method.

Method 1: Selected TC

Conversion of in vitro concentrations presented in TABLE 1 to dosages required to achieve in vivo epidermal concentrations would be performed by simple mathematical methods to achieve the desired concentrations in a given volume of skin. Normal epidermis is ~200 μm thick. The volume of epidermis per square centimeter of skin surface area is thus 20 cubic mm for normal epidermal thickness (10 mm×10 mm×0.2 mm). Converting this to ml at a rate of 1 cubic mm×1/1000 ml gives the respective volume in ml as 0.02 ml per square cm of skin surface area for normal epidermal thickness. The absolute amount of trichothecene to be administered per square cm of skin surface area to achieve the desired toxic concentration (TC), such as 100 ng/ml of satratoxin or roridin, can now be computed; 2 ng per square cm of skin surface area for normal thickness skin (i.e. 0.02 ml×100 ng/ml×2 ng). As an example, if a patient has a patch of ~1 square centimeter of discolored, but otherwise normal, epidermis they want to get rid of and they are using a 1000 ng/ml solution of Satratoxin or Roridin in ethanol, and want to achieve a TC of 100 ng/ml of epidermis, one would need to topically apply 0.02 ml (when the ethanol evaporates it leaves 2 ng in the 0.02 ml of epidermal volume or 100 ng/ml). The concentration or amount of the topical solution can be varied as desired as long as it leaves TC dose per square cm of skin to which it is topically applied.

Method 2: Selected Safety Level

Alternatively, does determination can be computed backwards from known safe levels, to determine the maximum therapeutic dose administrable. Preferred embodiment of present invention utilizes this approach for determining dosage.

Blood would be the primary transdermal entry point for the trichothecenes and insuring blood concentrations can never exceed a selected NTC level is the starting point of this method of dose determination. Both epidermal and bone marrow cells cycle on a roughly 24 hour clock and as such would be similarly susceptible to cytotoxicity. The average human has ~18 square feet of skin (17,000 sq. cm.). At a normal epidermal thickness of 200 $\mu$m this translates to 0.34 liters of epidermis. The average human contains ~5.5 liters of blood and 42 liters of extracellular water outside the vasculature (per HPIM). The small volume of epidermal human content (0.34 liters vs. 5.5 liters of blood) works in our favor. The blood circulates at roughly once every minute throughout the body in a resting state. Consequently, any trichothecenes that migrate into the blood would be almost instantly mixed into 5.5 liters of blood. A 10 ng/ml NTC in the blood this translates to 55,000 ng for the two macrocyclic trichothecenes and at 200 ng/ml translates into 1,100,000 ng/ml blood for the two simple trichothecenes. Furthermore, the dose guidelines outlined in present application use only 1% of these NTC levels for most applications (i.e. 500 ng and 10,000 ng, respectively) and only in the worst cases use 2% levels (i.e. 1000 ng and 20,000 ng, respectively) where large areas of epidermis are to be covered. Thus if for some reason 100% of the trichothecene were to directly enter the blood, the blood concentrations would be 100 times smaller and 50 times smaller, respectively, than known non toxic concentration levels.

A further safety check of these doses can be performed by contrasting the worst case 20,000 ng of T-2 used in present invention to AMRIID's computed LD50 (lethal dose to 50% of people) for T-2 by inhalation of 1.21 mg/kg of body weight. This LD50 translates to a 84,700,000 ng dose of T-2 being inhaled by a 70 kg person to have a 50% chance of survival (i.e the 20,000 worst case dose used is 4,200 times smaller). Magnuson et. al. cited a 2.0 mg/kg of body weight LD50 for topical application of T-2 in rats. Applying the rat model to humans would imply a 140,000,000 ng LD50 for topically applied T-2. Once again this is in stark contrast with the worst case 20,000 ng (7000 times smaller) maximum dose used by present invention. Furthermore, preferred embodiment of present invention favors macrocyclic trichothecenes which internalize more readily into epithelium because of their macrocyclic ring and tend to stay out of circulation because of their insolubility in blood versus simple trichothecenes such as T-2 that do not possess enhanced internalization afforded by the macrocyclic ring.

Even though the Cleveland Infant Model clearly demonstrates the proclivity of macrocyclic trichothecenes to internalize into epithelium they come into contact with, without appreciably entering general circulation, a worst case scenario is used in where 0% of the trichothecene is absorbed by the epidermis or dermis, and 100% enters the blood stream in constructing the dose tables below. Furthermore, the worst case maximum blood concentration we do not want to exceed is chosen at 1% of the known safe concentration of 10 ng/ml for satratoxin or roridin (i.e 0.01% level=0.1 ng/ml blood) and 200 ng/ml for T-2 or DAS (i.e.

1% level=2 ng/ml of blood) this means we can administer a dose containing up to 550 ng of satratoxin or roridin (0.1 ng/ml×5500 ml blood=550 ng) and a dose containing up to 11,000 ng of T-2 or DAS (i.e. 2 ng/ml×5500 ml blood=11,000 ng). For simplicity both maximum doses are reduced to 500 ng and 10,000 ng respectively for clinical use. The 500 ng dose would then be applied to a given volume of epidermis destined for chemexfoliation. Various concentrations of solution could be prepared to facilitate a single solution application regimen depending on depth of epidermis typical for the underlying condition. The appropriate amount of solution to be applied could be determined by simple mathematical computation for a given concentration of solution. As an example, if one square centimeter of epidermis is to be chemexfoliated and a 10,000 ng/ml solution (i.e. 500 ng/0.05 ml) of roridin or satratoxin in ethanol are being used, the amount to be applied would be 0.05 ml.—an amount which leaves 500 ng in the underlying epidermis. Likewise, if a 5,000 ng/ml solution of macrocyclics is used (i.e. 500 ng/0.1 ml) and only 1 sq. cm of epidermis is targeted for chemexfoliation, 0.1 ml of solution would be applied to the 1 sq. cm of epidermis.

As an example of simple trichothecenes, if 1 sq cm of epidermis is to be chemexfoliated and one is using a 100,000 ng/ml concentration of T-2 or DAS (10,000 ng/0.1 ml) in ethanol one would apply 0.1 ml to the square centimeter. If one is attempting to chemexfoliate 10 square centimeters of epidermis and is using the 100,000 ng/ml concentration one would need to apply the 0.1 ml of solution to the 10 square centimeters of skin or more appropriately use a 10,000 ng/ml solution and apply 1 ml of solution to the 10 square centimeters of skin. Some dosage examples are summarized in TABLE 2 below.

TABLE 2

Chemexfoliating Dose Table Example
(@ <1% of NTC in blood)

| Trichothecene | Safe Dose | Solution Concentration | Amount to Apply to Target Area |
| --- | --- | --- | --- |
| Roridin A | 500 ng | 10,000 ng/ml | .05 ml |
| Roridin A | 500 ng | 5,000 ng/ml | .10 ml |
| Satratoxin G | 500 ng | 10,000 ng/ml | .05 ml |
| Satratoxin G | 500 ng | 5,000 ng/ml | .10 ml |
| T-2 | 10,000 ng | 100,000 ng/ml | .10 ml |
| T-2 | 10,000 ng | 10,000 ng/ml | 1.0 ml |
| DAS | 10,000 ng | 100,000 ng/ml | .10 ml |
| DAS | 10,000 ng | 10,000 ng/ml | 1.0 ml |

These are only a few examples of the many possibilities that exist at the chosen<1% of NTC in blood, worst case dosages. Many different solution concentrations can be employed. Different safety levels can also be selected (i.e. <2% NTC in blood, <3% of NTC in blood, etc. . . . ) each with their own solution concentration combinations and administration amounts.

Since the start point for dose determination was at a given safety level, and administering is at a fixed dose over a variable area of skin, we need to work backward as to how much skin surface the dose may be applied to before the concentrations per ml of skin volume fall to the 10 ng/ml known non toxic level for roridin or satratoxin and 200 ng. for T-2 or DAS. A minimum efficacy level has been chosen at 10 times higher than the doses at which toxicity starts. As an example to maintain a TC≧100 ng/ml concentration of roridin or satratoxin for a given volume of normal epidermis (0.02 ml/sq cm) when administering a 500 ng dose, the amount of solution (per TABLE 2) cannot be applied to an area greater then 250 sq cm of skin surface in a single administration session (i.e. 500 ng÷100 ng/ml=5 ml of volume over which the 500 ng dose may be distributed and since 1 sq cm of normal skin has ~0.02 ml of epidermis, 5 ml of epidermis is contained in 5 ml÷0.02 ml/sq cm=250 sq. cm. of skin). This of course does not preclude the use of multiple application sessions, spaced 10 days or more apart, to insure inactivation of the trichothecenes before the next application session. TABLE 3 shows the maximum coverage area per session at the 1% NTC in blood for both normal thickness epidermis (0.2 mm) and thickened epidermis (1 mm) computed as described above.

TABLE 3

Maximum Chemexfoliation Area

| Trichothecene | 10% Dose | Min. Epidermal Efficacy Level | Max. Applic. Area (sq cm) |
|---|---|---|---|
| (Normal Thickness Epidermis = .02 ml/sq cm of skin) | | | |
| Roridin A | 500 ng | 100 ng/ml | 250 sq cm |
| Satratoxin G | 500 ng | 100 ng/ml | 250 sq cm |
| T-2 | 10,000 ng | 2000 ng/ml | 250 sq cm |
| DAS | 10,000 ng | 2000 ng/ml | 250 sq cm |
| (Thickened Epidermis = .1 ml/sq cm of skin) | | | |
| Roridin A | 500 ng | 100 ng/ml | 50 sq cm |
| Satratoxin G | 500 ng | 100 ng/ml | 50 sq cm |
| T-2 | 10,000 ng | 2000 ng/ml | 50 sq cm |
| DAS | 10,000 ng | 2000 ng/ml | 50 sq cm |

ADMINISTRATION EXAMPLES

Example 1

A patient presents with a wart on the back of their hand that they want removed. The wart is rounded with a base diameter of 5 mm an 3 mm high at the peak (note: the size of the wart is immaterial under method 2). Treatment: The 1% worst case blood NTC level is chosen, indicating a 500 ng macrocyclic dose to be administered, and a 5000 ng/ml solution of roridin in ethanol is used. The patient's hand is placed flat on a table with the wart pointing up. The wart is defatted with acetone. Petroleum jelly is applied around the wart to form a crater with the wart in the center of the crater. 0.1 ml of solution is applied into the crater by eve dropper, over a period of time to allow the dose to absorbed into the skin and ethanol to evaporate. Air flow and or heated air flow may be used to expedite the process.

Example 2

A patient presents with a wart on the back of their hand that they want removed. The wart is rounded with a base diameter of 5 mm an 3 mm high at the peak. Treatment: The 1% worst case blood NTC level is chosen, and a 100,000 ng/ml solution of T-2 is used to deliver the 10,000 ng dose. The patient's hand is placed flat on a table with the wart pointing up. The wart is defatted with acetone. Petroleum jelly is applied around the wart to form a crater with the wart in the center of the crater. 0.1 ml of solution is applied into the crater by eve dropper, over a period of time to allow the dose to absorbed into the skin and ethanol to evaporate. Air flow and or heated air flow may be used to expedite the process.

Example 3

A patient presents with a wart on the back of their hand that they want removed. The wart is rounded with a base diameter of 5 mm an 3 mm high at the peak. Treatment: The 1% worst case blood NTC level is chosen, and a 100,000 ng/ml solution of T-2 in ethanol is used to deliver a 5,000 ng dose of T-2 and a 5,000 ng/ml solution of satratoxin in ethanol is used to deliver a 250 ng dose of satratoxin. The patient's hand is placed flat on a table with the wart pointing up. The wart is defatted with acetone. Petroleum jelly is applied around the wart to form a crater with the wart in the center of the crater. 0.05 ml of the T-2 solution and 0.05 ml satratoxin solution is applied into the crater by eve dropper over a period of time to allow the dose to absorbed into the skin and ethanol to evaporate. Air flow and or heated air flow may be used to expedite the process.

Example 4

A patient presents with a brown mole on their arm they want removed. The mole is round with a base diameter of 5 mm and is 1 mm high and relatively flat. Treatment: A 0.5% worst case blood NTC level is chosen, and a 100,000 ng/ml solution of T-2 in ethanol is used to deliver a 2500 ng dose of T-2 and a 5,000 ng/ml solution of satratoxin in ethanol is used to deliver a 125 ng dose of satratoxin. The patient's arm is placed flat on a table with the mole pointing up. Any hairs are shaved or otherwise removed from the area. The mole is defatted with acetone and a piece of vinyl adhesive tape with a 0.6 mm hole punched out in it is stuck firmly onto the skin with the hole centered over the mole. 0.025 ml of the T-2 solution and 0.025 ml satratoxin solution is applied into the hole by eve dropper over a period of time to allow the dose to absorbed into the skin and ethanol to evaporate.

Example 5

A patient presents with age spots, actinic keratoses, pigmentary dyschromias, and aged skin on their face and would like a facial to rejuvenate the appearance of their skin. The area to be rejuvenated is ~300 sq. cm. Treatment: The 2% worst case blood NTC level is chosen (or any other suitable level), and a 200 ng/ml solution comprising 100 ng/ml roridin and 100 ng/ml satratoxin in ethanol (or any other suitable concentration or combination) is is used to deliver the 1,000 ng dose (or any other suitable dose). The patient is given an alpha hydroxy acid to apply the night before coming in to the facial. When the patient comes in their face is scrubbed with a loofah sponge or subjected to other available methods for removal of some of the uppermost portions of the epidermis. The patient's face is then defatted with acetone and petroleum jelly is applied to delicate parts that need to be protected. Appropriate eye protection is also placed on the patient The patient lies down on a table on their back. Five ml (or any other suitable amount) of solution is applied (e.g using a roller ball dispenser, brush, or any other suitable means) over the area of skin targeted for rejuvenation.

Example 6

A patient presents with with a patch of skin ~1 sq cm that is diagnosed to be squamous cell carcinoma. Treatment: The surface of the skin is abraded with a pumice stone to remove the upper part of the epidermis. An eye dropper is used to apply a 500 ng dose of Roridin A (0.1 ml of 5000 ng/ml solution) and a 10,000 ng dose of T-2 (0.1 ml of 100,000 ng/ml solution) (i.e. 2% hematologic safe level) over a roughly 4 sq. cm. area within which the 1 sq cm squamous cell cancer is centered.

Example 7

A patient presents with with a patch of skin ~1 sq cm that is diagnosed to be basal cell carcinoma. Treatment: The surface of the skin is abraded with a pumice stone to remove the upper part of the epidermis. An 4 cm diameter tube is pressed firmly against the skin and centered over the basal cell carcinoma. A 500 ng dose of Roridin A (1 ml of 500 ng/ml solution) and a 10,000 ng dose of T-2 (1 ml of 10,000 ng/ml solution) (i.e. 2% hematologic safe level) is poured into the tube. Positive air pressure is created inside the tube (e.g. by fitting a bulb over the open end and squeezing it, by inserting a plunger into the open end and pressing down on the plunger, by attaching an appropriate fitting and hose connected to a compressor, or any other suitable means) until the solution has been internalized by the skin.

Example 8

An AIDS patient has a 2 sq cm patch of skin exhibiting kaposi's sarcoma. The patient's CD4+ T cell count had fallen below 200 cells per microliter of blood and has remained below that level and is not likely to recover anytime soon. Meanwhile the kaposi's sarcoma continues to grow. Treatment: A 500 ng dose of Roridin A (0.1 ml of 5000 ng/ml solution) and a 10,000 ng dose of T-2 (0.1 ml of 100,000 ng/ml solution) (i.e. 2% worst case blood NTC level) is applied over a roughly 4 sq. cm. area within which the 2 sq cm kaposi's sarcoma is centered.

Preferred embodiment of present invention favors use of macrocyclic trichothecenes because the macrocyclic ring enhances cellular internalization and localization however nothing in this application or its related claims should be construed to limit use of simple trichothecenes or combinations of macrocyclic and simple trichothecenes. Combinations could be more efficacious than either alone as the macrocyclics would internalize more rapidly (higher concentration in upper layers) and the simple trichothecenes would penetrate deeper, concurrently the two could provide more uniform distribution through both upper and lower layers of the epidermis.

Present invention also envisions possible preparation of skin prior to administration of therapeutics of present inventions is also envisioned. Several pretreatment methods exist to facilitate deeper and more even distribution of substances and these generally involve removal of some of the uppermost portions of the epidermis. A simple mechanical removal of some of the outermost layers of psoriatic skin may be performed by simple mechanical abrasion with a pumice stone or loofah sponge. Alternatively, substances such as alpha of beta hydroxy acids may be applied prior to application of therapeutics. These acids dissolve the intercellular glue that hold cells together, allowing for better penetration of therapeutics of invention. Various types of alpha hydroxy acids (including lactic acid, citric acid, and glycolic acid) act in the upper layers of the epidermis to dissolve the intercellular glue. Beta hydroxy acid work in deeper layers of the epidermis. Lack of cellular attachment would facilitate profusion on therapeutic in the epidermis. Defatting skin with acetone prior to administration of therapeutics is used to facilitate uniform distribution of therapeutics.

Present invention also envisions directly incorporating any other substances into pharmaceutical compositions of present invention, such as those mentioned above that may facilitate application, enhance delivery or uniformity of distribution, or in any way increase efficacy into therapeutic compositions of present invention, including adding substances currently in use for topical epidermal chemexfoliation that function by alternative mechanisms of action or complementary mechanisms of action, previously described under prior art treatments section of this application (e.g. alpha or beta hydroxy acids), or any new such drugs to come onto the market in the future.

Nothing in this application is intended to limit additional compositions that may be added to or used in conjunction with pharmaceutical composition of present invention. Although therapeutics of present invention may be topically administered in any suitable solution (e.g. ethanol, methanol, propylene glycol, dimethyl sulfoxide) any other suitable agent, carrier or delivery vehicle may be use. A wide variety of compositions including antibiotics, antibiotic creams, or non-toxic pharmaceutical carriers or vehicles KY Jelly, or the like, and in any suitable form such as a liquid, solid, semi-solid, ointment, lotion, paste, or the like may also be used where advantageous. Heavier creams are specifically envisioned for home use type applications to make "idiot proof" pharmaceutical compositions that limit the dose of therapeutic that may be administered to a given area of skin.

Nothing in the application is intended to limit the devices and methods used to facilitate application or either therapeutics or pharmaceutical compositions of present invention. The examples of devices are only representative examples. Other devices, either currently existing, or to be developed in the future could also be employed. As an example devices (e.g. "atomizers") capable of accelerating therapeutics or pharmaceutical compositions of present invention to velocities capable of instantaneous epidermal penetration and distribution would in fact be a preferred delivery method in many applications.

It should also be recognized that, from a practical standpoint, more solution may need to be administered than presented in the examples to achieve the desired TC epidermal concentrations defined in present application. In the examples, the amount of trichothecene contained in the solution administered was set to match the dose required for the given epidermal volume for the sake of clarity. The concentrations were deliberately set very high, yet below chosen worst case "blood safe" levels, to make this issue a moot point.

Lastly, the concentrations used should not be construed as "optimal". As is customary under prior art, all dosages would be further refined and scrutinized by in vivo testing in suitable animal models or in Phase I and II clinical trials on humans as required by the FDA and the lowest concentrations suitable to achieve efficacy would likely be called "optimal". The "optimal" doses could readily be expected to be several times smaller than those presented in present application as well as being dependent on the skin preparations employed prior to administration. The doses presented in this application were done so to fulfill the reduction to practice requirement of this application and are not intended to imply an absolute standard or "optimal" dose but are merely some representative examples of efficacious, yet safe, embodiments of present invention.

REFERENCE CITED

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th or 15th edition, McGraw Hill, 1998/2000, Fauci, Braunwald, Isselbacher, Wilson, Martin, Kasper, Hauser, Longo.

I claim:

1. A method of chemexfoliating epidermal cells in humans or non-human animals, comprising topical application of composition containing a therapeutically effective amount of a trichothecene or a mixture of trichothecenes directly onto an area of skin to be chemexfoliated on said humans or non-human animals.

2. The method of claim 1 wherein said trichothecene is a fragment or sub-unit of trichothecene which possesses the ability to inhibit protein synthesis.

3. The method of claim 1 or 2 wherein the trichothecene compositions include a pharmaceutically acceptable carrier.

4. The method of claim 3 wherein the pharmaceutically acceptable carrier is selected from the group consisting of propylene glycol, ethanol, methanol, and dimethyl sulfoxide.

* * * * *